United States Patent
Bare

(10) Patent No.: US 8,269,571 B2
(45) Date of Patent: ***Sep. 18, 2012

(54) AMPLITUDE MODULATED PULSE TRANSMITTER

(76) Inventor: James E. Bare, Albuquerque, NM (US)

(*) Notice: Subject to any disclaimer, the term of this patent is extended or adjusted under 35 U.S.C. 154(b) by 611 days.

This patent is subject to a terminal disclaimer.

(21) Appl. No.: 12/457,502

(22) Filed: Jun. 12, 2009

(65) Prior Publication Data

US 2009/0310709 A1 Dec. 17, 2009

Related U.S. Application Data

(60) Provisional application No. 61/129,243, filed on Jun. 13, 2008.

(51) Int. Cl.
*H03C 1/02* (2006.01)
*H03C 1/36* (2006.01)
*H04L 27/04* (2006.01)

(52) U.S. Cl. ........ 332/149; 332/155; 332/173; 332/176; 332/178; 375/268; 375/300; 455/108

(58) Field of Classification Search .................. 332/103, 332/105, 149, 155, 167, 168, 170, 173, 176–178; 375/268, 270, 298, 300, 301, 353; 455/108, 455/109

See application file for complete search history.

(56) References Cited

U.S. PATENT DOCUMENTS

| | | | | |
|---|---|---|---|---|
| 3,706,038 A | * | 12/1972 | Austin et al. | 375/309 |
| 6,717,504 B2 | * | 4/2004 | Fujiwara et al. | 336/233 |
| 7,574,186 B2 | * | 8/2009 | Turner | 455/264 |
| 7,750,749 B2 | * | 7/2010 | Jones | 332/105 |
| 2010/0049261 A1 | * | 2/2010 | Bare | 607/1 |

* cited by examiner

*Primary Examiner* — Levi Gannon
(74) *Attorney, Agent, or Firm* — Welsh Flaxman & Gitler LLC

(57) ABSTRACT

An amplitude modulated pulse transmitter designed to operate across a multi MHz range of modulation frequencies. A wire wound rare earth magnet is to be utilized instead of the typical modulation transformer. Additionally, a plurality of electrolytic capacitors are also employed in the transmitter.

13 Claims, 2 Drawing Sheets

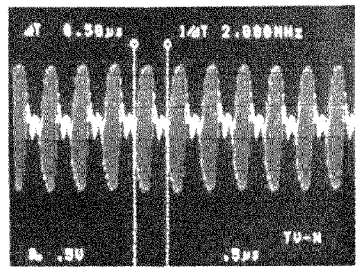
Figure 1
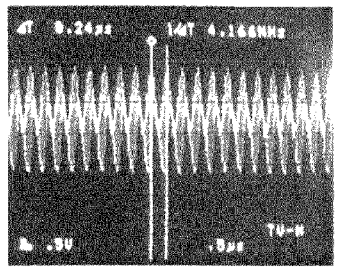
Figure 2
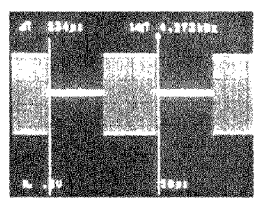
Figure 3
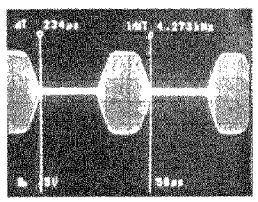
Figure 4
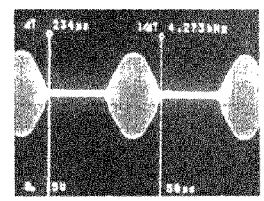
Figure 5
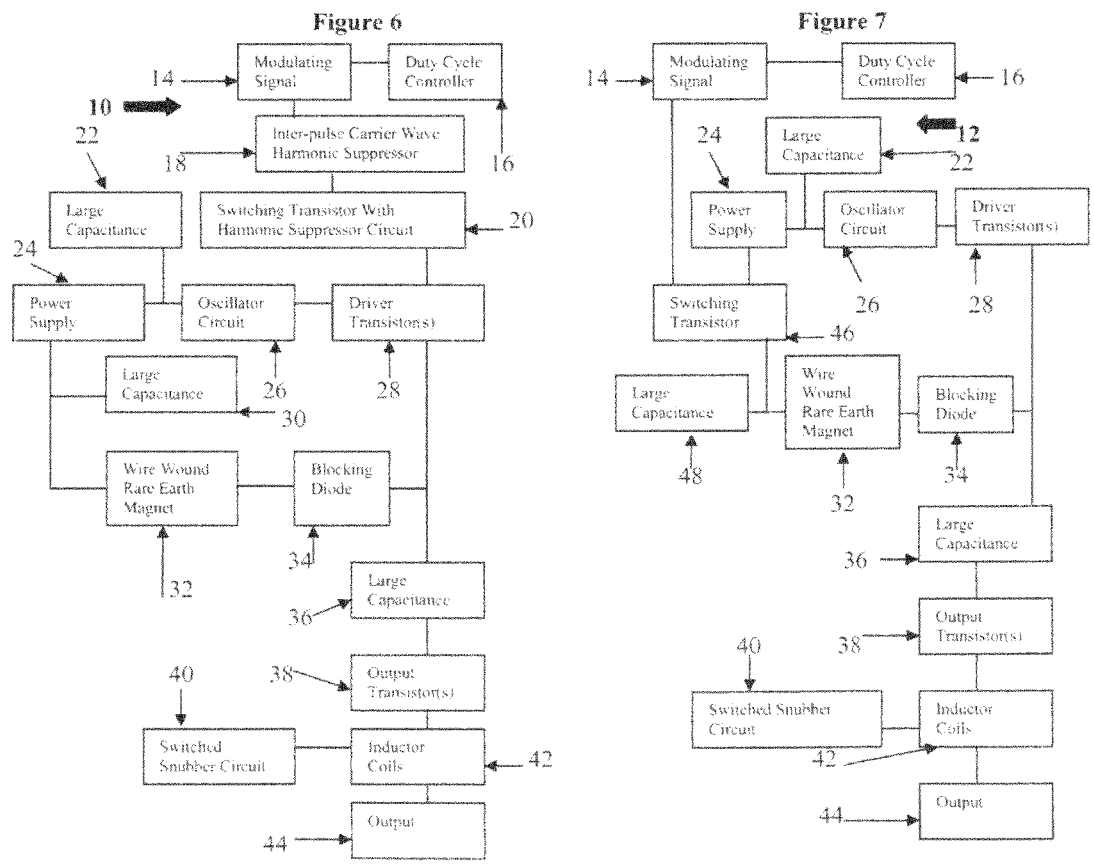

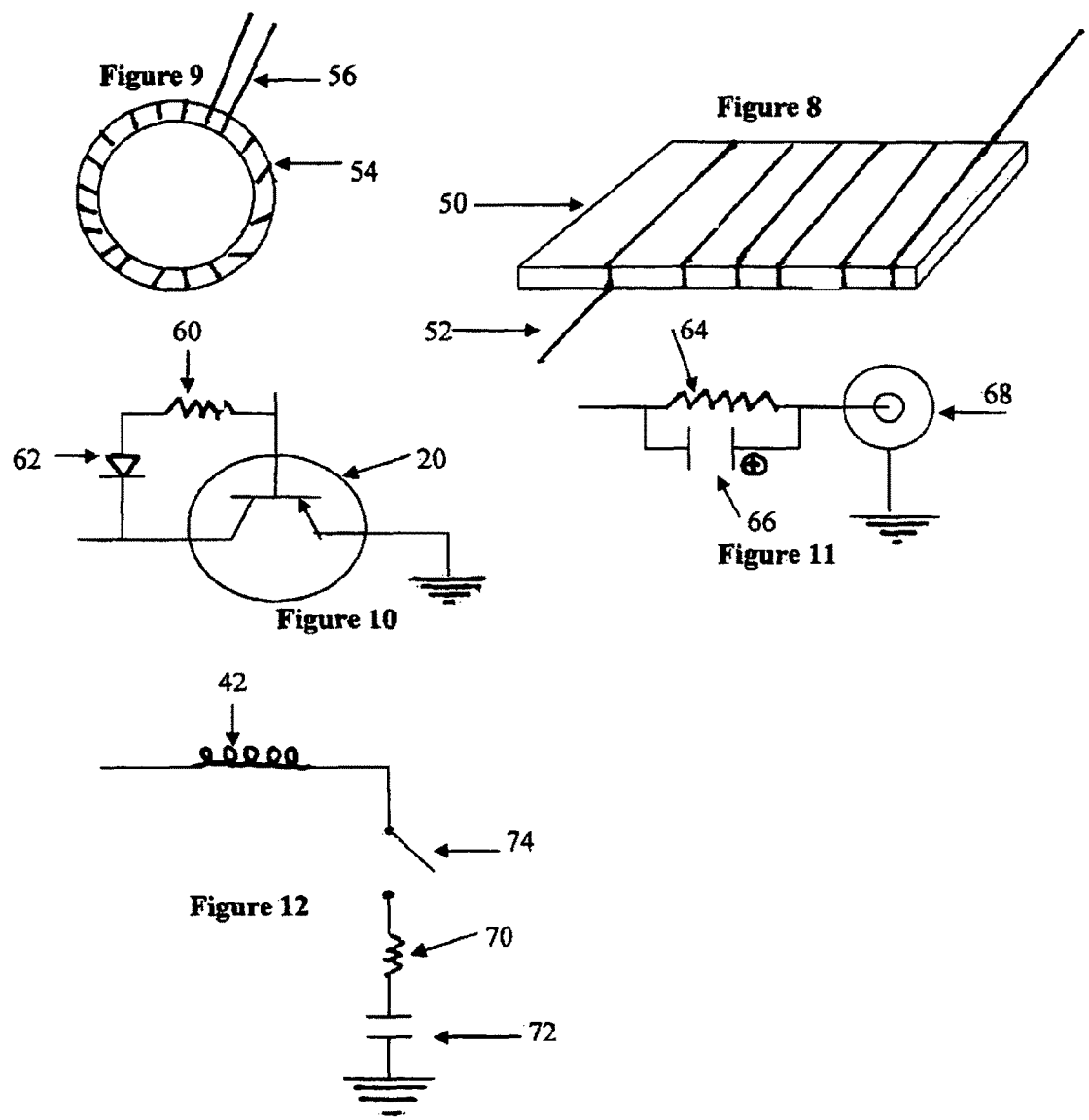

AMPLITUDE MODULATED PULSE TRANSMITTER

CROSS-REFERENCE TO RELATED APPLICATION

The present patent application claims the priority of U.S. provisional patent application Ser. No. 61/129,243, filed on Jun. 13, 2008, and incorporates the material therein by reference.

FIELD OF THE INVENTION

The present invention is directed to an amplitude modulated (AM) radio transmitter able to modulate electrical signals in the range of 1 Hz to a megahertz (MHz) range of 4 MHz or greater. The transmitter has applications to the use of radar, data transmission, laser power source as well as biophysiologic affects extending to all types of multi cellular organisms, single organisms, plant life, viruses and cell types including cancer.

BACKGROUND OF THE INVENTION

Pulse mode amplitude modulated (AM) radio transmission of MHz pulse repetition rates by a transmitter, is well known in the prior art. The majority of AM pulse transmitters are not designed for variable MHz frequency bandwidth modulation. Most AM pulse transmitters, whether of fixed or variable carrier frequency, are designed to operate within a very narrow (few tens or hundreds of KHz) modulation frequency range.

A variable pulse rate amplitude modulated transmitter of wide modulation bandwidth is subject to several attributes which are difficult to design. RC and LC charge and discharge constants, as well as circuit reactance can affect the modulation frequency bandwidth and pulse shape. Ideally, wide band width modulation capability will need very short (nanosecond range or shorter) RC and LC time constants. As pulse frequencies, or pulse bandwidth increases, circuit reactance increase, causing significantly diminished output power levels. Increased reactance that occurs with large increases in modulation frequency can cause an imbalance of the output impedance value. It is important to keep the output impedance static (generally 50 ohms) regardless of modulation frequency. A pulse transmitter of fixed carrier frequency that produces maximum output power at 2 KHz modulation frequency may produce very little output power with a 2 MHz modulation frequency. Circuit reactance is a direct function of frequency, a 1000 times change in frequency is accompanied by a 1000 times change in reactance. Large swings in circuit reactance cause unstable output impedances. Stable output impedance is necessary for connection of the transmitter to accessory components such as a power amplifier or an antenna.

SUMMARY OF THE INVENTION

The transmitter of the present invention is designed to generate modulated pulse transmissions from less than one Hz to several millions of Hz (MHz). The transmitter can be of either a fixed or variable carrier frequency. Pulse duration can therefore extend from greater than one second in duration to shorter than 100 nanoseconds in duration. The LC and RC time constants are optimized to operate at high modulation frequencies. In order to overcome problems with changes in circuit reactance and output impedance values with changes in modulation frequency, this transmitter offers a unique component and circuit for holding reactance values and impedance in balance through a wide (Multi-MHz) pulse frequency range.

The transmitter of the present invention generates a pulse mode AM radio wave. Although similar to what is known as gated carrier transmission—such as used in Morse Code, this transmitter is designed as a form of pulsed high level Amplitude Modulation. In a gated carrier, the carrier output power is held constant and then turned on and off at the applied pulse rate. Output power tends to be stable with changes in frequency.

In what is known as high level gated Amplitude Modulation, the un-modulated carrier power is held constant at a relatively low value, while modulated carrier output power level is adjusted by variations in the modulating frequency, modulating voltage, and modulating current. The output power of the transmitter is therefore not solely dependent upon the power (wattage) of the un-modulated carrier wave. This transmitter is designed to operate with a fixed modulation voltage level. That is, the voltage of the modulating signal is kept constant. Only the modulating frequency and modulating current is varied. Variation of the modulating frequency can create variability in the output power of the transmitter, by creating variation in the current demand. For example, the power output (into a 50 ohm load) of the transmitter with an un-modulated carrier may be only 2 to 4 watts. When modulated, the output power can climb to almost 60 watts average transmitter power output at modulation frequencies above 40 KHz. At modulation frequencies of below 40 KHz, power will diminish. As an example at 20 Hz, the output power of the transmitter may only be 8 watts average transmitter power output.

The unique ability to maintain output impedance values and manage circuit reactance in this transmitter means that maximum power output and standing wave ratios (SWRs) stay very flat up to modulation frequencies around 1 MHz. Above 1 MHz modulation frequencies (pulse repetition rate or PRR), there will be a gradual drop off in power output and slight increase in SWR up to about 5 MHz. At 5 MHz power output may be only 30 to 40 watts average transmitter output power, and SWR may increase by about 0.2 to 0.3. FIG. 1 shows the transmitter pulse output at a 2 MHz pulse rate. FIG. 2 illustrates the transmitter pulse output at a 4.1 MHz pulse rate.

FIG. 2 illustrates the transmitter pulse output at a 4.1 MHz pulse rate. The pulsed AM transmitter according to the present invention may be created via the following method:

An oscillator circuit generates a carrier frequency, and is designed to be constantly on when power is applied to the transmitter. For simplification, the word "Transistor" here can mean a standard bipolar RF transistor or an FET transistor. If an FET is used, for simplicity of explanation the term "Collector" for this circuit unless other wise stated, will mean either the Drain or the Source depending upon whether or not multiple or single FET's are used in the driver and output circuits. In a normal high level AM transmitter circuit, a modulation transformer is used to provide high voltage and current to the collectors of the driver and output transistor(s). In this circuit, there is no modulation transformer. Therefore, a separate power supply is used instead of the modulation transformer to provide constant voltage and variable current to the collectors of the driver and output transistor(s) in lieu of the modulation transformer. The present invention utilizes a unique combination of a wire wound rare earth magnet as well as a number of large capacitors in the circuit. The voltage supplied to the collectors of the driver and output transistor(s)

is about 2 times that supplied to the carrier frequency oscillator circuit. Both the carrier oscillator circuit, and the driver and output transistor(s) have a common ground connection. By controlling the emitter to ground connection of the driver transistors (or source of an FET) with a square wave via a fast switching transistor, the circuit is enabled and a pulse is generated.

The transmitter of the present invention outputs an enhanced pulse mode AM modulation so that it is capable of MHz bandwidth ranges of pulse generation via a square wave modulation which would produce a rectangular pulse as shown in FIG. 3. As illustrated in FIG. 4, modulation with a sine wave would create an oval shaped pulse. Modulation with a triangle wave as shown in FIG. 5 would create a trapezoidal shaped pulse. By utilizing a wave shaper for modulation, a very wide variety of RF pulse envelope shapes can be created.

However, regardless of the type of wave used for modulation, the output transmission would always be a series of pulses. The pulse shape occurs as the ratio of the carrier wave module of voltage to the modulating wave voltage. This ratio results in severe overmodulation which is beyond 100%. Severe overmodulation provides in a pulse output regardless of the modulating wave form. Duty cycles above 50% depending upon the modulating wave type may limit the frequency response of the circuit. Some modulating wave shapes and types may need a reduced duty cycle below 50% in order for the output of the transmitter to be a pulse when utilizing MHz level modulation frequencies.

At times it may be necessary for a generated pulse to be shorter than a certain time duration, for example 1 microsecond. Nanosecond time duration pulses have uses in data transmission, radar, and with cellular biological process manipulation. An ideally shaped 500 KHz pulse at 50% duty cycle will have a duration of 1 microsecond. Adjustment of the duty cycle is capable of significantly shortening the pulse time duration. By using a duty cycle of 25%, a 500 KHz pulse will have a time duration of 500 nano seconds. At a modulation frequency of 5.5 MHz, and 25% duty cycle, a measured pulse can be generated of 100 ns.

By adjustment of the duty cycle, the transmitter is capable of generating pulses shorter than 1 microsecond using modulation frequencies as low as 100 KHz. As the transmitted pulse rate increases (consider modulating square wave duty cycle fixed), the number of carrier wave oscillations in each transmitted pulse envelope decreases. The transmitted pulse envelope becomes shorter in duration as the frequency increases. For example with a carrier wave of 27 MHz, there would be approximately 5 carrier oscillations in each transmitted pulse envelope when the transmitter is square wave modulated with a 2.7 MHz 50% duty cycle square wave. The number of carrier oscillations in each pulse envelope is also dependent upon the duty cycle of the square wave. Duty cycles above 50% will produce more carrier oscillations in each pulse envelope. Duty cycles below 50% will produce fewer carrier oscillations in each pulse envelope.

With a 50% duty modulation square wave, one finds that modulation frequencies above 10% of the carrier frequency have very few carrier oscillations within the pulse envelope and may result in diminished usefulness or effectiveness of the transmission. To remedy this, one could utilize a higher carrier frequency. Higher carrier frequencies would enable faster rise/fall times to the pulse envelope, and also higher useful modulation frequencies. For example, a carrier frequency of 500 MHz would allow for modulation frequencies at least as high as 50 MHz.

Gating of the modulation frequency will create two demodulation frequencies. Frequency one would be the primary modulation frequency for an example 100 KHz. This 100 KHz signal may then be gated—for example at 1 KHz. This would create a situation wherein a 27 MHz carrier wave is modulated at 100 KHz and then gated at 1 KHz, thereby simultaneously transmitting the modulated frequencies.

The transmitter may be designed to utilize a very low carrier wave frequency. As the carrier frequency decreases, the generated harmonics of the carrier wave and side bands if modulated) are closer together. For example with a carrier wave at 27.12 MHz (an ISM frequency) harmonics are generated at 27.12 MHz intervals. With a carrier frequency of 6.78 MHz (another ISM frequency) harmonics are generated every 6.78 MHz. This would produce bandwidth coverage of the generated side bands that occurs with lower carrier frequencies. Should the carrier frequency be low enough, and the modulation frequency be high enough, there will be a nearly continuous coverage of the frequency spectrum between the carrier harmonics. It has been found that biophysiologic effects can be enhanced by both an increase in harmonics within the side bands, and an increase in the number of carrier frequency harmonics within a specified bandwidth. For example in the bandwidth from 0 to 217 MHz, there will be about 8 carrier harmonics generated using a carrier of 27.12 MHz. If one uses a carrier of 6.78 MHz, there would be almost 32 carrier harmonics generated within the 217 MHz bandwidth. Each harmonic will have a set of side bands. Side bands formation is not just related to the modulation frequency but also a function of the rise time of the pulse envelope. Fourier transformation states that the number of harmonics and thus side bands possible are roughly related to the mathematical function of [1/rise time]. As the rise time diminishes, the number of harmonics increases.

Increased numbers of carrier harmonics and sidebands within a specific frequency bandwidth, results in increased physiologic effect capability. Testing revealed that a standing wave is generated in the high voltage power input line that supplies the collectors of the driver and output transistors. This standing wave moves back and forth within the power wire based upon the modulation frequency, the modulating signal (square wave, triangle wave, sine wave, etc.) and the duty cycle of the modulating signal. When a rare earth magnet of high gauss capability is placed over the standing wave, the standing wave will be influenced to the benefit of the transmitter's operation. Primarily, circuit reactance, transmitter output power, and output impedance is affected in a very positive manner. In prior art pulse mode AM transmitters, as modulation frequency increases, the transmitted pulse generated tends to degrade in shape and output power diminishes. Frequency response of the circuit tends to drop off as well. This is due to several factors. These are the aforementioned LC and RC time constants, circuit reactance, and also an irregularity of the energy available in each carrier wave oscillation that makes up the pulse.

BRIEF DESCRIPTION OF THE DRAWINGS

For a fuller understanding of the reference, reference is made to the following description taken in connection with the accompanying drawings in which the same elements in the various drawings maintain the same reference numeral.

FIG. 1 is a graph showing the transmitter pulse output of the present invention and a 2 MHz pulse rate;

FIG. 2 is a graph showing the transmitter pulse output at a 4.1 MHz pulse rate;

FIG. 3 is a graph showing a square wave modulation;

FIG. 4 is a graph showing a sine wave modulation;

FIG. 5 is a graph showing a triangle wave modulation;

FIG. 6 is a block diagram showing a first embodiment of the amplitude modulated pulse transmitter;

FIG. 7 is a block diagram of a second embodiment of the amplitude modulated pulse transmitter;

FIG. 8 shows one type of rare earth magnet used in the present invention;

FIG. 9 shows a second type of rare earth magnet utilizing the present invention;

FIG. 10 shows the switching transistor used in the present invention;

FIG. 11 shows the harmonic suppressor circuit utilized in the first embodiment of the present invention; and FIG. 12 shows the switched snubber circuit used in both embodiments of the present invention.

DETAILED DESCRIPTION OF THE PRESENT INVENTION

FIGS. 6 and 7 illustrate two embodiments of the amplitude modulated pulse transmitter, the similarities and the differences will be described herein below. As shown in these figures, a modulated signal 14 is introduced into the either of the transmitting circuits 10, 12. The duty cycle of this signal would be controlled by a standard duty cycle controller 16.

Both of the transmitters 10, 12 would utilize a wire wound rare earth magnet 32 instead of a transformer used in a standard AM modulated pulse transmitter. Typical of the rare earth magnets utilized in the present invention are shown in FIG. 8 which employs a bar magnet having a wire 52 wrapped therearound in a sequential manner. A ring magnet 54 is illustrated with respect to FIG. 9. The ring magnet 54, similar to the bar magnet 50, would include a wire wrap 56. Each of the rare earth magnets would have a high gauss rating and is wound a number of times with their respective wires 52, 56. It is preferable that these wires be made of solid copper to create a type of circular magnetic inductor. As shown in FIG. 6, the rare earth magnet 32 is directly connected between a standard power supply 24 and a blocking diode 34. This is the high power side of the transmitter circuit which would supply voltage and current to the collector's source (FET) of the driver transistor or transistors 28 as well as the output transistor or transistors 38.

It has been determined that the number of turns of the wire in either the bar magnet 50 or the ring magnet 54 would affect the operation of the transmitters 10, 12. For example, utilizing a ring magnet having a 0.75 inch diameter, a suitable range of turns would be between 15 and 25. Based upon the sizes and shapes (square, rectangular and so forth) the number of magnets, as well as the different sizes of wire, different circuits and different strengths of magnets will cause a variation in the number of necessary turns. Employing the high gauss rare earth magnets, many of the circuit's reactances are eliminated and the output power tends to stay very flat with increases in modulation frequencies. Output impedance stays very constant with only slight variations across a multi MHz wide modulation frequency range.

The pulse shaped, frequency response and irregularity of each carrier oscillation in the pulse is corrected by stabilizing the pulse shape at high frequencies. This is accomplished utilizing the large capacitors 22, 30 and 36 of FIG. 6 as well as the large capacitors 22, 36 and 48 of the circuit illustrated with respect to FIG. 7. It has been found that electrolytic capacitors having a range of 3300 uf to approximately 10,000 uf are added to improve the pulse shape and frequency response. The capacitor 22 in both circuits is provided in parallel to the low voltage input 24 of the power supply that powers an oscillator circuit 26. A second large electrolytic capacitor 30 having the same parameters of the capacitor 22 is provided in parallel to the high voltage input side of the circuit between the power supply 24 and the rare earth magnet 32. The large capacitor 48 of FIG. 7 is provided between the power supply 24 and the rare earth magnet 32 through a switching transistor 46. In this second embodiment, the modulated signal is directly connected to the switching transistor 46. A third large electrolytic capacitor 36 having the same parameters as the first and second large capacitors is added in series to the circuit that feeds the collector (FET source) of the driver transistor or transistors 28 and the base (FET-Gate) of the output transistor or transistors 38 in both FIGS. 6 and 7.

It is important to note that the large capacitor 36 is installed backwards with the negative side of the capacitor receiving positive power from the high voltage side of the circuit that feeds the collectors of the output transistor or transistors 38. The positive side of this capacitor is attached to the collector or collectors of the drive transistor or transistors 28 and to the base of the output transistor or transistors. Installing this capacitor 36 backwards decreases the rise and fall time of the pulse envelope. Additionally, the voltage rating of the capacitor must be significantly higher than that of the voltage entering it. It is important to note that use of a non-polar electrolytic capacitor in this position results in a slight degradation of rise and fall time pulse envelope shaping and modulation frequency capability can be employed. Use of these high value capacitors will improve the pulse shape; assist in stabilizing output power level of the transmitter and increase pulse frequency bandwidth. The capacitor 36 must have a significantly higher voltage rating than would normally be used in this type of transmitter. For example, a 30 volt capacitor might be used if installed normally. In this case, a 100 volt rating or more must be used. If a non polar electrolytic capacitor is used, the voltage of the capacitor can be set for the circuit (30 volts).

Prior art high level AM modulated pulse transmitters would use a modulation transformer. In this case, a blocking diode was used to prevent ingress of RF energy into the modulation transformers. Both of the circuits shown in FIGS. 6 and 7 would use a similar blocking diode 34 to limit RF entry back to the power supply after passing through the rare earth magnets 32. This blocking diode plays an important role in the modulation pass band and impedance stabilization ability of the transmitter. The diode 34 is connected to the source of the driver transistors 28 and the output transistors 38 and the electrical parameters of the diode is important to the operation of the transmitter. An incorrect diode would cause a limit of the pass band, a degradation of the pulse shape, a limit to the duty cycle response at high KHz and MHz frequencies, as well as slow rise and fall time. The blocking diode 34 would have a low forward resistance which can effect the RC time which can affect the pass band and pulse shape, the circuit reactance which affect the pass band as well as the circuit reactance which effect the transmitter output impedance variation with modulation frequency. The RC as well as LC time constants are calculated utilizing the following: The RC time constant is identified by the Greek letter $\tau$. The time constant is given in seconds. $\tau = R \times C$ Where R is the circuit resistance in ohms and C is the circuit capacitance in farads. The cutoff frequency or $f_c$ is the maximum frequency a circuit will pass and is related to τ. Cutoff frequency is calculated in this manner.

$$\tau = RC = \frac{1}{2\pi f_c}$$

or $$f_c = \frac{1}{2\pi RC} = \frac{1}{2\pi\tau}$$

The LC time constant is derived by the formula
Time=L/R Where L is inductance in Henry's and R is the resistance in Ohms and Time is in seconds.

The cutoff frequency is the maximum frequency the circuit will pass, and what is wanted is a high cut off frequency. At MHz pulse rates times get very short—billionths of a second. As can be seen, it is the combined values of R, C, or L, which can increase, or if one is not careful, decrease the cut off frequency. In this transmitter—one must be careful of how the values are combined. What is wanted are very high MHz cut off frequencies. The transmitter is capable of generating pulses of 100 nanosecond or 100 billionths of a second duration. This all applies to the blocking diode. Diodes have voltage losses across them due to internal resistances, as well as on/off switching time, which both play a part in the transmitters pulse rate capability.

Increasing voltage of the low voltage side of the circuit which includes the oscillator, to a value approximately 50 to 60% of the high voltage side of the circuit decreases the rise and fall time of the pulse, increases output power across the transmitters pulse bandwidth, improves pulse envelope shape, and decreases ringing of the pulse. For example the high voltage side of the circuit that feeds the collectors (FET-Source) of the output transistors may be operating at 31 volts, while the low voltage side of the circuit would be operated at 16 volts.

Increasing the current to the low voltage side of the circuit, which includes the oscillator, while holding the voltage at a low level (13 Volts typical) will produce an effect similar to that of increasing the voltage. That is, an increase in current will increase output power across the transmitter bandwidth, improve pulse envelope shape, and decrease ringing of the pulse. The advantage of increasing current over increasing voltage of the low voltage—oscillator side of the circuit, is that when using an amplifier with a high conduction angle, the carrier wave will not fully cut off between pulses, and the carrier will tend to be of significant enough power between pulses to damage an amplifiers transistors. As such, a low voltage with high current improves the ability of the transmitter to be used with an amplifier.

Circuit ringing between pulses can become evident at modulation frequencies of 1 MHz and above. This is important since the range of the transmitter of the present invention can be as great as 4 MHz and above. If severe enough, the circuit ringing can cause limitation of the pulse bandwidth capability. One manner in which this situation can be alleviated would be to utilize a harmonic suppressor 18 with a switching transistor 20 in the first embodiment illustrated with respect to FIG. 6. This switching transistor along with the harmonic suppressor circuit is illustrated in FIG. 10. The switching transistor 20 is utilized with a resistor 60 and a diode 62. The resistor is approximately 12 ohms and one end is connected to the base of the switching transistor 20. The other end of the resistor 60 is attached to the anode of the diode 62. The cathode of the diode is connected to the collector of the switching transistor 20.

Another manner of controlling the circuit ringing is to use a switched snubber circuit 40 as illustrated in FIG. 12. The snubber circuit can be used with both the transmitters shown in FIGS. 6 and 7. This circuit includes a resistor 70 and capacitor 72 provided in series with one end of the capacitor attached to ground. The resistor and capacitor are connected in series to a tuning inductor coil 42. The coil 42 or coils are provided between the output transistor 38 and an output jack 44. Additionally, switch 74 is provided between the coils 42 and the snubber circuit 40.

The circuit illustrated in FIG. 6 also includes an inter-pulse carrier wave harmonic suppressor 18 as illustrated in FIG. 11. This circuit would eliminate the inter-pulse carrier wave harmonic form by utilizing a small resistor 64 and an electrolytic capacitor 66 between the modulation signal input jack and the switching transistor 58. The small resistor could be of approximately 50 ohms and the electrolytic capacitor would be about 20 uf placed in parallel to each other and in series with the input modulation signal 68 before the signal is sent to the base of the switching transistor 58. The positive end of the electrolytic capacitor 66 is attached to the input side of the wave signal. The use of this arrangement would eliminate damage to power transistors that would be used in an attached amplifier.

The circuit shown in FIG. 7 is quite similar to the circuit shown in FIG. 6 with several variations. Both circuits have fast rise and fall times, multi MHz modulation frequency bandwidths and control the circuit reactance and impedances. In this variation, the circuit is arranged so that there is a constant low wattage carrier signal generated by the transmitter even when no modulation is present. In this variation, the emitter to ground connection of the driver transistors is connected directly to ground and the inter-pulse carrier wave harmonic suppressor 18 and the switching transistor 20 provided in FIG. 6 are eliminated. A low voltage equal to the voltage transmitted to the oscillator circuit 26 is fed continuously to the collectors of the driver transistors 28 as well as the output transistors 38. This would provide for a constant low power output that should be equal to that are required by an attached amplifier. The transistors and many amplifiers require four to five watts to fully drive the transistors in the amplifier. This would be the typical output power to the transmitter shown in FIG. 7 in an unmodulated state, but could be more or less depending upon the needs of the amplifier. The power provided into the rare earth magnet 32 would be controlled by separate solid state switch such as a MOSFET or a fast switching transistor 46. The modulating signal is used to switch the power on with the voltage about twice the voltage of the oscillator circuit 26 to the rare earth magnet 32 and then feed their power to the collectors of the drive transistors 28 and output transistors 38.

When the output 44 of the transmitter in each of the embodiments is connected to an antenna or device designed specifically to utilize RF energy, the transmitter can be used to produce bio-physiologic effects which are well known attributes of EM fields found in the prior art. Affects that extend to all types of single and multi cellular organisms, or plant life, viruses, single and multi cellular microorganisms, and cell types such as cancer. These affects can be detrimental or beneficial depending upon several parameters, such as modulation frequency, exposure time, field strength and antenna emission spectra.

When the transmitter uses a carrier frequency suitable for these purposes and is connected to a metal antenna with or without power amplification, it can be used for data transmission using pulse mode communication. It also could generate pulses uses for radar signal emissions as well as to drive a suitable laser tube and thus create a pulse light emission of MHz frequency capabilities.

It will be seen that some changes can be made from the description of the transmitters of the present invention that are apparent from this description and can be obtained without departing from the spirit and scope of the invention. It is therefore intended that all matter contained in the above description and shown in the accompanying drawings shall be interpreted as illustrative and not in a limiting sense.

What is claimed is:

1. An amplitude modulated pulse transmitter, comprising:
    a modulated signal producing device providing a modulating signal;
    at least one driver transistor;
    an oscillator circuit connected to said at least one driver transistor;
    a power supply having a high voltage side connected to said oscillator circuit;
    a wire wound rare earth magnet connected to said power supply and said modulated signal producing device;
    at least one output transistor in communication with said wire wound rare earth magnet and said at least one driver transistor; and
    an output jack in communication with said at least one output transistor;
    wherein the amplitude modulated pulse transmitter provides a modulated pulse output without the utilization of a transformer.

2. The amplitude modulated pulse transmitter in accordance with claim 1, further including a first electrolytic capacitor connected backwards between said at least one driver transistor and at least one output transistor with the positive side of said capacitor connected to the collector or collectors of said at least one driver transistor and the negative side of said first electrolytic capacitor receiving positive power on the high voltage side of said power supply, thereby decreasing the rise and fall time of the pulse envelope produced by the transmitter.

3. The amplifier modulated pulse transmitter in accordance with claim 2, further including a blocking diode provided between said wire wound rare earth magnet and said first capacitor.

4. The amplitude modulated pulse transmitter in accordance with claim 3, further including a second electrolytic capacitor provided between said power supply and said wire wound rare earth magnet and a third electrolytic capacitor in parallel between said power supply at said oscillator circuit.

5. The amplitude modulated pulse transmitter in accordance with claim 4, wherein said first, second and third capacitors have values of between 3300 uf and 10,000 uf.

6. The amplitude modulated pulse transmitter in accordance with claim 5, further including a duty cycle controller connected to said modulated signal producing device, wherein output pulse shorter than 1 microsecond can be produced using modulation frequencies as low as 100 KHz.

7. The amplitude modulated pulse transmitter in accordance with claim 1, wherein said wire wound rare earth magnet is a bar magnet wound with a plurality of turns of solid copper magnet wire.

8. The amplitude modulated pulse transmitter in accordance with claim 1, wherein said wire wound rare earth magnet is ring shaped as is provided with between 15 and 25 turns of a solid copper magnet wire.

9. The amplitude modulated pulse transmitter in accordance with claim 6, further including a harmonic suppressor and switching transistor provided between said modulated signal producing device and said at least one driver transistor.

10. The amplitude modulated pulse transmitter in accordance with claim 6, further including a switching transistor provided in parallel with said second electrolytic capacitor and said wire wound rare earth magnet.

11. The amplitude modulated pulse transmitter in accordance with claim 10, wherein said switching transistor is a MOSFET.

12. The amplitude modulated pulse transmitter in accordance with claim 9, further including switch and snubber circuit and at least one inductor coil between said at least one output transistor and said output jack.

13. The amplitude modulated pulse transmitter in accordance with claim 10, further including switch and snubber circuit and at least one inductor coil between said at least one output transistor and said output jack.

* * * * *